(12) United States Patent
Yacovan et al.

(10) Patent No.: US 11,427,545 B2
(45) Date of Patent: Aug. 30, 2022

(54) PROCESS FOR THE PREPARATION OF QUINMERAC

(71) Applicant: ADAMA AGAN LTD., Ashdod (IL)

(72) Inventors: Avihai Yacovan, Mazkeret Batya (IL); Omer Tzor, Kiryat-Ono (IL)

(73) Assignee: ADAMA AGAN LTD., Ashdod (IL)

( * ) Notice: Subject to any disclaimer, the term of this patent is extended or adjusted under 35 U.S.C. 154(b) by 62 days.

(21) Appl. No.: 17/254,952

(22) PCT Filed: Jun. 24, 2019

(86) PCT No.: PCT/US2019/038727
§ 371 (c)(1),
(2) Date: Dec. 22, 2020

(87) PCT Pub. No.: WO2020/005830
PCT Pub. Date: Jan. 2, 2020

(65) Prior Publication Data
US 2021/0147362 A1    May 20, 2021

Related U.S. Application Data

(60) Provisional application No. 62/689,235, filed on Jun. 24, 2018.

(51) Int. Cl.
*C07D 215/48* (2006.01)

(52) U.S. Cl.
CPC .................................. *C07D 215/48* (2013.01)

(58) Field of Classification Search
None
See application file for complete search history.

(56) References Cited

U.S. PATENT DOCUMENTS 4,715,889 A * 12/1987 Hagen .................. C07D 215/48
504/225

* cited by examiner

*Primary Examiner* — Samantha L Shterengarts
(74) *Attorney, Agent, or Firm* — Browdy and Neimark, PLLC

(57) ABSTRACT

It is an object of the present invention to provide a novel and advantageous process for commercially preparing quinmerac.

12 Claims, No Drawings

PROCESS FOR THE PREPARATION OF QUINMERAC

FIELD OF THE INVENTION

The present invention concerns an improved process for preparation of 7-chloro-3-methyl-8-quinolinecarboxylic acid, known by the name Quinmerac.

BACKGROUND OF THE INVENTION

Quinmerac, known by the chemical name 7-chloro-3-methyl-8-quinolinecarboxylic acid is represented by the following formula (I).

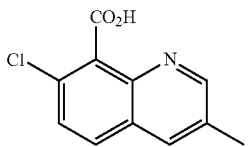

(I)

Quinmerac is a synthetic auxin. It induces formation of 1-aminocyclopropane-1-carboxylic acid, leading to ethylene formation which induces the formation of abscisic acid (K. Grossmann & F. Scheltrup, *Proc. Br. Crop Prot. Conf.— Weeds,* 1995, 1, 393).

The use of Quinmerac as an herbicide is described in European patent EP104389.

The synthesis of quinolinecarboxylic acid by subjecting an anthranilic acid to a Skraup cyclization reaction is known (Monatsh 2 1981, 518). However, the yields are frequently low, especially in the case of 8-quinoline carboxylic acids, this is due to partial decarboxylation under reaction conditions.

U.S. Pat. No. 4,715,889 describes the preparation of quinolones via bromination of quinolone and oxidation of the methyl group. The oxidation results in relatively low yields and lots of waste.

In view of the aforementioned, there is a need for an improved process for preparing of Quinmerac represented as a compound of formula (I), which will be suitable for industrial scale, highly efficient, low-cost, environmentally friendly, and provides a higher yield and easy workup, thereby overcoming the deficiencies of the prior art.

SUMMARY OF THE INVENTION

The present invention provides a process for preparation of Quinmerac represented by the following formula (I):

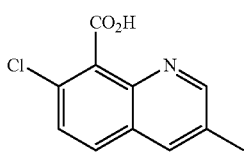

(I)

which process comprises reacting 2-amino-6-chlorobenzonitrile represented by the following formula (II):

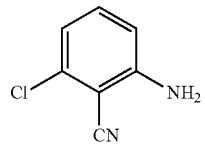

with methacrolein, in the presence of an acid and an oxidizing agent.

The present invention further includes a process for the preparation of 7-chloro-3-methyl-8-quinolinecarboxylic acid represented by the following formula (I):

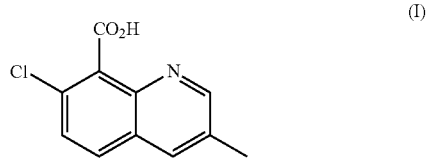

(I)

which process comprises reacting 2-amino-6-chlorobenzonitrile represented by the following formula (II):

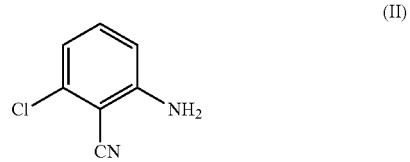

(II)

with methacrolein, in the presence of an acid, an oxidizing agent and at least one co-oxidant.

DETAILED DESCRIPTION OF THE INVENTION

Definitions

Prior to setting forth the present subject matter in detail, it may be helpful to provide definitions of certain terms to be used herein. Unless defined otherwise, all technical and scientific terms used herein have the same meaning as is commonly understood by one of skill in the art to which this subject matter pertains.

The term "a" or "an" as used herein includes the singular and the plural, unless specifically stated otherwise. Therefore, the terms "a," "an," or "at least one" can be used interchangeably in this application.

Throughout the application, descriptions of various embodiments use the term "comprising"; however, it will be understood by one skilled in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages, or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques. In this regard, use of the term "about" herein specifically includes ±10% from the indicated values in the range. In addition, the endpoints of all ranges directed to the same component or property herein are inclusive of the endpoints, are independently combinable, and include all intermediate points and ranges.

Preparation of Quinmerac:

The present invention provides a process for preparation of Quinmerac represented by the following formula (I):

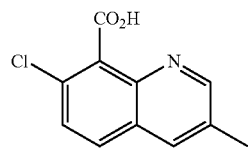

(I)

which process comprises reacting 2-amino-6-chlorobenzonitrile represented by the following formula (II):

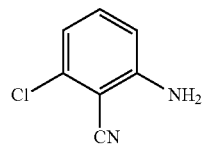

(II)

with methacrolein, in the presence of an acid and an oxidizing agent.

In an embodiment of the invention the acid is selected from the group consisting of sulfuric acid and hydrochloric acid.

In a specific embodiment the acid is sulfuric acid.

In an embodiment of the present processes, the molar ratio between the compound of formula (II) to the acid is from about 1:1 to about 1:50. In another embodiment, the molar ratio between the compound of formula (II) to the acid is from about 1:1 to about 1:25.

In a specific embodiment, the molar ratio between the compound of formula (II) to the acid is about 1:10.

In another specific embodiment the molar ratio between the sulfuric acid and the compound of formula (II) is about 10:1.

In an embodiment, the oxidizing agent is selected from the group consisting of nitrobenzene, nitromethane, sodium nitrate and sodium 3-nitrobenzenesulfonate.

In an embodiment water is added to the reaction.

The reaction of the present invention can further comprise an organic solvent. Non limiting examples of organic solvents include toluene, xylene, chlorobenzene.

In an embodiment of the invention the reaction is carried out at a temperature of from 100 to 160° C.

In another embodiment of the invention the molar ratio of the compound of formula (II) to the methacrolein is from about 1:1 to about 1:10. In another embodiment, the molar ratio between the compound of formula (II) to the methacrolein is from about 1:1 to about 1:2.

In a specific embodiment, the molar ratio between the compound of formula (II) to the methacrolein is about 2:1.

According to an embodiment, the process of preparation of compound represented as formula (I) may be carried out at a temperature of from about 100° C. to 160° C., preferably of from about 140° C. to 160° C.

According to an embodiment, the molar ratio of the compound of formula (II) to the oxidizing agent is from about 1:1 to 1:5, preferably 1:2.

In another embodiment, the present invention provides a process for the preparation of 7-chloro-3-methyl-8-quinolinecarboxylic acid represented by the following formula (I):

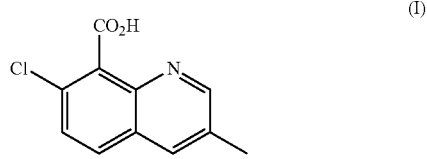

(I)

which process comprises reacting 2-amino-6-chlorobenzonitrile represented by the following formula (II):

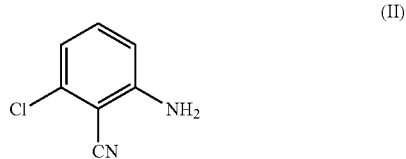

(II)

with methacrolein, in the presence of an acid, an oxidizing agent and at least one co-oxidant.

In an embodiment water is added to the reaction.

In yet another embodiment the reaction further comprises an organic solvent.

In an embodiment the acid is selected from a group consisting of sulfuric acid and hydrochloric acid.

In a specific embodiment the acid is sulfuric acid.

In an embodiment the co-oxidant is selected from a group consisting of Iron(II) sulfate and Boric acid.

In a specific embodiment of the invention the co-oxidant is a mixture of Iron(II) sulfate and Boric acid.

In an embodiment of the present processes, the molar ratio between the compound of formula (II) to the acid is from about 1:1 to about 1:50. In another embodiment, the molar ratio between the compound of formula (II) to the acid is from about 1:1 to about 1:25.

In a specific embodiment, the molar ratio between the compound of formula (II) to the acid is about 1:10.

In another specific embodiment the molar ratio between the sulfuric acid and the compound of formula (II) is about 10:1.

In an embodiment, the oxidizing agent is selected from the group consisting of nitrobenzene, nitromethane, sodium nitrate and sodium 3-nitrobenzenesulfonate.

The reaction of the present invention can further comprise an organic solvent. Non limiting examples of organic solvents include toluene, xylene, chlorobenzene.

In an embodiment of the invention the reaction is carried out at a temperature of from 100 to 160° C.

In another embodiment of the invention the molar ratio of the compound of formula (II) to the methacrolein is from about 1:1 to about 1:10. In another embodiment, the molar ratio between the compound of formula (II) to the methacrolein is from about 1:1 to about 1:2.

In a specific embodiment, the molar ratio between the compound of formula (II) to the methacrolein is about 2:1.

According to an embodiment, the process of preparation of compound represented as formula (I) may be carried out at a temperature of from about 100° C. to 160° C., preferably of from about 140° C. to 160° C.

According to an embodiment, the molar ratio of the compound of formula (II) to the oxidizing agent is from about 1:1 to 1:5, preferably 1:2.

The following examples are presented in order to illustrate certain embodiments of the invention. They should in no way, however, be construed as limiting the broad scope of the invention. One skilled in the art can readily devise many variations and modifications of the principles disclosed herein without departing from the spirit and scope of the invention.

EXAMPLE

Raw Materials Consumption on 2.0 g Scale

| Name | Mw | Equivalent | g/batch (ml/batch) |
|---|---|---|---|
| 2-amino-6-chlorobenzonitrile | 152.58 | 1.0 | 2.00 g |
| methacrolein | 70.09 | 2.0 | 1.84 g |
| boric acid | 61.83 | 1.0 | 0.81 g |
| conc. $H_2SO_4$ | 98.08 | 10.0 | 12.86 g |
| $FeSO_4 \cdot 7H_2O$ | 278.01 | 0.2 | 0.73 g |
| nitrobenzene | 123.11 | 2.0 | 2.70 ml |
| water | — | — | 4.80 ml |

All reagents including 2-amino-6-chlorobenzonitrile can be bought from Sigma-Aldrich.

General Procedure

To a suspension of 2.00 g (13.1 mmol) of 2-amino-6-chlorobenzonitrile, 0.81 g (13.1 mmol) of boric acid, 12.86 g (131.1 mmol) of conc. $H_2SO_4$, 0.73 g (2.6 mmol) of $FeSO_4 \cdot 7H_2O$, 2.70 ml (26.2 mmol) of nitrobenzene and 4.80 ml of water, 2.16 ml (1.84 g; 26.2 mmol) of methacrolein was added dropwise over 90 min at 100° C. Then the reaction mixture was stirred at 130° C. over 6 h. Reaction mixture was cooled and poured into 50 g of ice-water. Precipitate was filtered off and pH of the filtrate was brought to 3 with saturated sodium hydroxide solution, while cooling in ice bath. Solid was filtered, washed with cold water and dried in vacuo. Then the solid was triturated with hexane, filtrate and dried to give 2.20 g of light-brown solid.

Isolated yield: 76%

NMR purity: 94%

The invention claimed is:

1. A process for the preparation of 7-chloro-3-methyl-8-quinolinecarboxylic acid represented by the following formula (I):

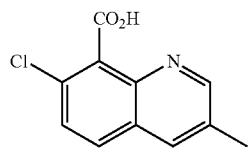

(I)

which process comprises reacting 2-amino-6-chlorobenzonitrile represented by the following formula (II):

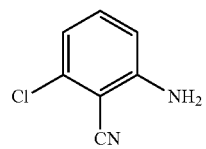

(II)

with methacrolein, in the presence of an acid and an oxidizing agent and optionally at least one co-oxidant.

2. The process according to claim 1, wherein the acid is selected from the group consisting of sulfuric acid and hydrochloric acid.

3. The process according to claim 1, wherein the oxidizing agent is selected from a group consisting of nitrobenzene, nitromethane, sodium nitrate, sodium 3-nitrobenzenesulfonate.

4. The process according to claim 1, wherein the reaction further comprises an organic solvent selected from a group consisting of toluene, xylene, chlorobenzene.

5. The process according to claim 1, wherein the reaction is carried out at a temperature of from 100 to 160° C.

6. The process according to claim 1, wherein the molar ratio of the compound of formula (II) to the methacrolein is from about 1:1 to about 1:10.

7. The process according to claim 6, wherein the molar ratio of the compound of formula (II) to the methacrolein is about 1:2.

8. The process according to claim 1, wherein the molar ratio of the compound of formula (II) to the oxidizing agent is from about 1:1 to about 1:5.

9. The process according to claim 8, wherein the molar ratio of the compound of formula (II) to the oxidizing agent is 1:2.

10. The process according to claim 1, wherein the molar ratio of the compound of formula (II) to the acid is from about 1:1 to about 1:50.

11. The process according to claim 10, wherein the molar ratio of the compound of formula (II) to the acid is 1:10.

12. The process according to claim 1, wherein the co-oxidant is selected from a group consisting of Iron(II) sulfate and/or Boric acid.

* * * * *